United States Patent [19]

Kurozumi et al.

[11] 4,008,125

[45] Feb. 15, 1977

[54] NEW CYCLOPENTENE-DIOLS AND NEW ACYL ESTERS THEREOF AND PROCESS FOR THEIR PREPARATION

[75] Inventors: Seizi Kurozumi; Takeshi Toru; Toshio Tanaka; Shuzi Miura; Makiko Kobayashi; Sadakazu Matsubara, all of Hino; Sachio Ishimoto, Tokyo, all of Japan

[73] Assignee: Teijin Limited, Osaka, Japan

[22] Filed: Nov. 10, 1975

[21] Appl. No.: 630,711

[30] Foreign Application Priority Data

Dec. 26, 1974 Japan .......................... 49-148263
Dec. 26, 1974 Japan .......................... 49-148266
Mar. 13, 1975 Japan .......................... 50-29486
Apr. 17, 1975 Japan .......................... 50-45793
Apr. 18, 1975 Japan .......................... 50-46525
Apr. 21, 1975 Japan .......................... 50-47408

[52] U.S. Cl. .............................. 195/51 R; 195/30
[51] Int. Cl.$^2$ ........................................ C12D 13/02
[58] Field of Search ........................... 195/30, 51 R

[56] References Cited

UNITED STATES PATENTS 3,773,622   11/1976   Sih ........................................ 195/30
3,892,630   7/1975   Kurozumi et al. .................... 195/30

*Primary Examiner*—Alvin E. Tanenholtz
*Attorney, Agent, or Firm*—Sherman & Shalloway

[57] ABSTRACT

New optically active cyclopentene-diol and the mono- or diacyl esters thereof and a process for converting a diacyl ester of cyclopent-1-en-3,5-diol to its monoacyl ester and/or its diol which comprises subjecting a diacyl ester of cyclopent-1-en-3,5-diol containing at least one of the optically active or inactive diacyl ester of trans-cyclopent-1-en-3,5-diol (trans-isomer) and diacyl esters of cis-cyclopent-1-en-3,5-diol (cis-isomer), to the action of a microorganism or enzyme having at least a selectivity in its rates of hydrolyzing the acyloxy group (R) configuration and the acyloxy group (S) configuration of said diacyl ester.

These new compounds are valuable as starting materials for the preparation of prostaglandin or its analogues.

10 Claims, No Drawings

NEW CYCLOPENTENE-DIOLS AND NEW ACYL ESTERS THEREOF AND PROCESS FOR THEIR PREPARATION

This invention relates to new cyclopentene-diols and new acyl esters thereof and a process for preparing these compounds.

More particularly, this invention relates to a new optically active cyclopentene-diol and the monoacyl and diacyl esters thereof and a process for the preparation of these compounds.

Further, the present invention concerns a process wherein the diacyl esters of cyclopent-1-en-3,5-diols are subjected to the action of microorganisms or enzymes to convert said diacyl esters to the monoacyl esters and/or diols thereof.

The cyclopentene-diols and their mono- or diacyl esters are, for example, compounds which are valuable as starting materials for drugs used in the preparation of prostaglandin or its analogues, which have been attracting attention in recent years. In view of the fact that prostaglandin exhibits pharmacological activities over a broad range such as hypotension control, smooth muscle contraction, anti-inflammatory, platelet aggregation inhibiting and gastric secretion inhibiting activities, etc., it is being watched with great interest in the field of medicine, drugs or chemistry. In addition, the cyclopentene-diols or the derivatives thereof that are obtained by the process of this invention are also valuable as intermediates for perfumes or the pyrethroid type agricultural chemicals and their analogues.

The diacyl esters of cyclopent-1-en-3,5-diols of the following formula (I)

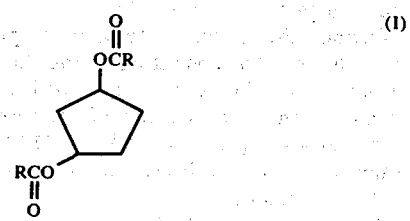

wherein R is a monovalent hydrocarbon residue of 1–10 carbon atoms, have the following three classes of stero-configurational isomers; namely:

I-A. A diecyl ester of (R)-trans cyclopent-1-en-3,5-diol[hereinafter referred to as (R)-trans-diester, at times] of the following formula (I-A)

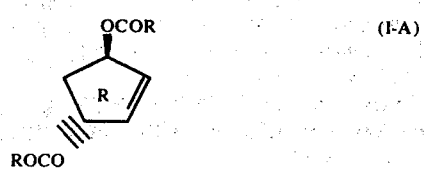

I-B. A diacyl ester of (S)-trans-cyclopent-1-en-3,5-diol [hereinafter referred to as (S)-trans-diester, at times] of the following formula (I-B)

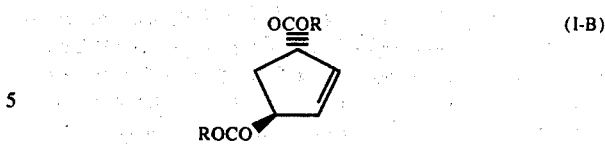

I-C. A diacyl ester of cis-cyclopent-1-en-3,5-diol [hereinafter referred to as cis-diester, at time] of the following formula (I-C)

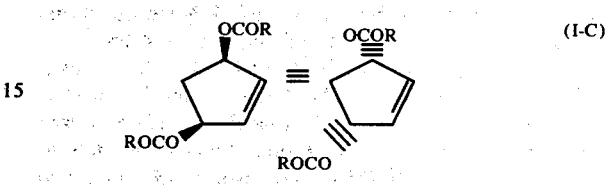

The foregoing (R)-trans-diester of formula I-A and (S)-trans-diester of formula I-B are optically active compounds, but the cis-diester of formula I-C is an optically inactive compound (meso-isomer).

As is apparent from the stereo-configurational isomers of the foregoing diesters, the monoesters and diols obtained, say, by hydrolyzing the foregoing diesters, also have the following stero-configurational isomers.

Monoacyl esters

II-A. Monoacyl ester of (R)-trans-cyclopent-1-en-3,5-diol[hereinafter referred to as (R)-trans-monoester, at times].

II-B. Monoacyl ester of (S)-trans-cyclopent-1-en-3,5-diol [hereinafter referred to as (S)-trans-monoester, at times].

II-C. 3(S)-acyloxy-5(R)-hydroxy-cyclopent-1-ene [hereinafter referred to as 3(S)-cis-monoester, at times].

II-D. 3(R)-acyloxy-5(S)-hydroxy-cyclopent-1-ene [hereinafter referred to as 3(R)-cis-monoester, at times].

All of the foregoing compounds II-A through II-D are optically active.

Diols

III-A. (R)-trans-cyclopent-1-en-3,5-diol[hereinafter referred to as (R)-trans-diol, at times].

III-B. (S)-trans-cyclopent-1-en-3,5-diol[hereinafter referred to as (S)-trans-diol, at times].

III-C. Cis-cyclopent-1-en-3,5-diol[hereinafter referred to as cis-diol, at times].

Of these diols, the foregoing trans-diols of III-A and III-B are optically active compounds, but the foregoing cis-diol of III-C is expressed by the same formula as that of the foregoing diester of I-C and is a compound that is optically inactive.

It has been known to prepare the aforesaid diacyl esters of cyclopent-1-en-3,5-diol by, say, such methods as (i) that of heat-treating 1,4-dibromocyclopent-2-ene with a potassium salt of an aliphatic carboxylic acid of 1–10 carbon atoms such as potassium acetate; (ii) that of treating 1,4-dibromocyclopent-2-ene in an aliphatic carboxylic acid of 1–10 carbon atoms with a silver salt of said carboxylic acid under conditions of heating; and (iii) that of reacting 1,4-dibromocyclopent-2-ene with a tetraethylammonium salt of said aliphatic carboxylic acid in acetone [L. N. Owen and Smith, *J. Chem. Soc.* (1952) 4035].

Further, the diacyl estes (I) can also be prepared in accordance with a process suggested by us, a process consisting of a solution of 1,4-dibromocyclopent-2-ene in an inert organic solvent difficulty soluble in water with an aqueous solution of a metal salt of said aliphatic acid in the presence of a cationic surface active compound [T. Toru, S. Kurozumi et al., *Synthesis* (1974) 867].

However, when the 1,4-dibromocyclopent-2-ene is crystallized and separated, it is possible to separate the cis-isomer, but the trans-isomer cannot be separated. Hence, it is not possible to directly prepare the trans-diacyl ester (IA + IB) by the foregoing processes.

Again, while it is possible, though difficult, to separate the cis-isomer and the trans-isomer by precise fractional distillation from the diacyl ester (I) prepared by the foregoing various methods, it was impossible to separate the optically active trans-isomer of said diacyl ester (I) by any of these methods.

It is therefore an object of this invention to provide from the diacyl ester of optically inactive cyclopent-1-en-3,5-diol[diacyl ester (I)] optically active diacyl esters or optically active monoesters thereof or optically active diols.

Another object of the invention is to provide at least one optically active new compound selected from the group consisting of the aforementioned compounds of (R)-trans-diester (I-A), (S)-trans-diester (I-B), (R)-trans-monester (II-A), (S)-trans-monoester (II-B), 3(S)-cis-monester (II-C), (R)-trans-diol (III-A) and (S)-trans-diol (III-B) or a new optically active composition containing these new compounds in higher concentrations, as well as a process for preparing these new compounds and compositions.

A further object of this invention is to provide a new process by which at least one of either the foregoing diacyl esters (I), their optically inactive trans-isomers or their optically inactive cis-isomers are hydrolyzed.

A still another object of this invention is to provide a method of further enhancing the optical purity of the aforesaid di- or monoester composition containing at least one of either said optically active trans-di- or monoester or cis-monoester.

An additional object of the invention is to provide a process by which at least one of the aforesaid optically active diester, monoester or diol is produced while carrying out the foregoing hydrolysis.

Other objects and advantages of the invention will become apparent from the following description.

The foregoing objects and advantages of the invention are achieved by submitting a diacyl ester of cyclopent-1-en-3,5-diol containing at least either an optically active or inactive diacyl ester of trans-cyclopent-1-en-3,5-diol(trans-isomer) or diacyl ester of cis-cyclopent-1-en-3,5-diol (cis-isomer) of the following formula

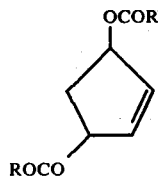

wherein R is a hydrocarbon residue of 1–10 carbon atoms, to the action of either a microorganism or enzyme having at least a selectivity in the hydrolysis rate between the acyloxy group of (R) configuration and the acyloxy group of (S) configuration to convert the diacyl ester of cyclopent-1-en-3,5-diol to its monoacyl ester and/or its diol.

Further, in accordance with this invention, the diacyl esters containing at least one of either a diacyl ester of (R)-trans-cyclopent-1-en-3,5-diol [(R)-trans-diester (I-A)] or a diacyl ester of (S)-trans-cyclopent-1-en 3,5-diol [(S)-trans-diester (I-B)] can be submitted in a culture medium to the action of either a microorganism or an enzyme having a selectivity in the hydrolysis rate between the acyloxy group of (R) configuration and the acyloxy group of (S) configuration to accumulate at least said (R)-trans-diester (I-A) and said (S)-trans-diester (I-B) in said medium as esters or diols of differing degrees of acylation, thereby selectively hydrolyzing said (R)-trans-diester (I-A) and(S)-trans-diester (I-B) and, as desired, separating and recovering at least one of said selectively hydrolyzed (R)-trans-isomer and (S)-trans-isomer from said culture medium.

The diacyl esters of cyclopent-1-en-3,5-diol conveniently used in the invention process as the starting material are those containing 1. the diacyl ester of (R)-trans-cyclopent-1-en-3,5-diol[(R)-trans-diester] and
2. the diacyl ester of (S)-trans-cyclopent-1-en-3,5-diol[(S)-trans-diester] and, in addition,
3. the diacyl ester of cis-cyclopent-1-en-3,5-diol (cis-diester).

However, the starting materials are not limited to those indicated above but may also be those containing 1'. the (R)-trans-monoester (II-A) and
2'. the (S)-trans-monoester (II-B) and, in addition,
3'. the cis-diester (I-C) or its optically active cis-monoesters (II-C, II-D).

In these cases, the proportions of the (R)-trans-diester to the (S)-trans-diester and the (R)-trans-monoester to the (S)-trans-monoester of the starting material may be of any value desired.

Further, the starting material of the present invention may also be that consisting of the diacyl ester of cis-cyclopent-1-en-3,5-diol. When this is submitted to the action of the aforementioned microorganism or enzyme, cis-cyclopent-1-en-3,5-diol (III-C) or its monoesters (II-C and/or II-D) can be accumulated in the culture medium.

As methods of hydrolyzing the esters with microorganisms, known heretofore are such methods as that of hydrolyzing the cyclopentenone derivatives with the *Saccharomyces* species as proposed by William J. Marsheck and Masateru Miyano [see *Biochimica et Biophsia Acta* 316,363 (1973)], that of hydrolyzing 15-deoxyprostaglandin $E_1$ ethyl ester with baker's yeast as suggested by Charles J. Sih et. al. [see *Journal of Chemical Society, Chemical Communication*, 240 (1970)], or that of hydrolyzing prostaglandin $E_1$ methyl ester with *Rhizopus Oryzae* as suggested by Charles J. Sih et al. [see *Journal of American Chemical Society*, 97, 857 (1975), 97, 865 (1975)].

However, the hydrolysis of the diacyl esters of 1-cyclopenten-3,5-diol with microorganisms is not known at all.

The present invention will be described more fully hereinafter.

As the aforementioned diacyl esters, which are used as the starting material in this invention, conveniently usable are those in which the R in the aforementioned formula (I) is an alkyl radical of 1–5 carbon atoms, especially advantageous being that in which R is methyl. When this invention is applied to the diacyl esters which have been partially hydrolyzed by the invention process or other chemical processes, in such cases also convenient is that in which the R is an alkyl radical of 1–5 carbon atoms, e.g., methyl, ethyl, propyl, isopropyl, butyl, t-butyl, pentyl and monochloromethyl, especially preferred being that in which R is methyl.

Conveniently usable as the microorganisms in this invention are the yeasts belonging to the *saccharomyces* species, and especially the yeasts belonging to *Saccharomyces Cerevisiae* which is known as the commercially available baker's yeast.

On the other hand, the enzymes conveniently usable in this invention include, for example, (A) the hydrolytic enzyme contained in the rind of citrus fruits, (B) the filamentous fungus belonging to the genus Aspergillus or the hydrolytic enzyme obtained from the metabolic product thereof, and (C) the hydrolytic enzyme contained in wheat germ.

Especially convenient as the hydrolytic enzyme of (A), above, is citrus acetyl esterase, while as the hydrolytic enzyme of (B), above, suitable is the filamentous fungus belonging to *Aspergillus Niger* or the hydrolytic enzyme obtained as a metabolic product thereof. On the other hand, wheat germ lipase is conveniently usable as the hydrolytic enzyme of (C), above.

1. The case where use is made of a yeast belonging to the *Saccharomyces* species According to this invention, when a culture medium containing the aforesaid diacyl ester (I), a typical starting material, is inoculated with a yeast belonging to the *Saccaromyces* species, preferably baker's yeast, it is possible by utilizing especially the difference in the rates by which said yeast hydrolyzes the acyloxy group of (R) configuration of the trans-isomer and the acyloxy group of (S) configuration of the trans-isomer, i.e., selectivity in the rates by which the yeast hydrolyzes the (R) and (S) positions of the trans-diester, to accumulate in the culture medium at least one compound of the group consisting of (i) the diacyl ester of (R)-trans-cyclopent-1-en-3,5-diol[(R)-trans-diester(I-A)], (ii) the monoacyl ester of (R)-trans-cyclopent-1-en-3,5-diol[(R)-trans-monoester (II-A)] and (iii) (S)-trans-cyclopent-1- en-3,5-diol[(S)-trans-diol (III-B)].

Hence, according to this invention, at least one of these compounds I-A, II-A and III-B that have been accumulated in the culture medium can be separated and recovered therefrom. Again, it is also possible, if desired, to recover a composition containing at an enhanced concentration at least one of the foregoing compounds I-A, II-A and III-B. All of these compounds I-A, II-A and III-B are optically active stereo-configurational isomers.

Furthermore, since both the compounds I-A and II-A are isomers that are convertible to (R)-trans-diol (III-A), it becomes possible by separating the foregoing compounds I-A and II-A from compound III-B to finally separate the (R)-trans-diol and the (S)-diol.

As the culture medium to be inoculated with the aforesaid yeasts, any can be usually used so long as it is one that can cultivate yeasts. For Example, usable are those mentioned in *Kobo no Bunrui Koteiho* (Identification methods of yeasts) Todai Shuppankai, p. 38 and *Pan Kobo* (Baker's yeast), Tomotaro Sato, ed., Korinshoin. Again, such a culture medium is also mentioned in the following literatures; R. P. Lanzilotta, D. G. Brudley, and K. M. McDonald Applied Microbiology, 27, 130 (1974). W. J. Marsheck and M. Miyano, Biochim, Biophsica Acta, 316, 363 (1973).

When using resting cells of such a yeast, any aqueous solution in which the cells can remain dormant, such as deionized water or a buffer solution can be used as the solution in which to disperse the cells. However, the method in which an aqueous solution containing glucose and monobasic sodium phosphate is preferred because of its high conversion of the substrate.

As methods of inoculating the foregoing yeasts, such modes as the following can be mentioned.

1. A method of inoculating a culture medium containing the substrate with the yeast cells and carrying out the cultivation of the cells therein.

2. A method of carrying out the cultivation of the yeast cells by gradually adding the substrate as the growth of the cells take place.

3. A method consisting of first cultivating the yeast cells and thereafter contacting the latter as resting cells with the substrate.

Of these methods, that of (3) is preferred because of its high conversion of the substrate. The substrate is used in such a concentration as will permit the growth of the yeast cells, the preferred concentration being about 0.05–25% by weight based on the culture liquid. On the other hand, in the case where the resting cells are to be used in accordance with the method of (3), the concentration of the substrate is suitably about 1.0 – 20% by weight based on the weight of the yeast cells As previously mentioned, the yeasts belonging to the *Saccharomyces* species, and especially baker's yeast, possess a selectivity in their rates of hydrolyzing the acyloxy groups of (R) and (S) configurations of especially trans-isomers of the aforementioned diacyl ester (I). However, in consequence of our researches, it has now been found that the hydrolyzing rate of the cis-isomer was the fastest, while the rates of hydrolysis of the (S)-trans-isomer and the (R)-trans-isomer were slower in the order given.

Hence, it becomes possible according to this invention to optically divide the aforesaid optically inactive diester (I) by utilizing this difference in hydrolytic rates and by suitably adjusting the reaction time, say, the innoculation time of said yeast, and the conditions of inoculation.

Further, as is apparent from the foregoing actions, it can be appreciated that the invention process is not limited in its application to substrates which are optically inactive, i.e., a mixture consisting of equal amounts of the trans-isomer and the cis-isomer but can also be applied to that in which one or the other is somewhat less, i.e., a substrate of low optically purity. A substrate of this kind can be obtained, say, by utilizing the difference in the hydrolytic rates by application of the invention process to a diacyl ester of cyclopent-1-en-3,5-diol abounding in the trans-isomer and then recovering this.

Thus, an optical isomer of high optical purity can be obtained by repeatedly applying the present invention in accordance with the mode described above.

If, by way of example, the instance where a diacyl ester of cyclopent-1-en-3,5-diol is used as the substrate is described, the cis-diester (I-C) disappears in 9–12 hours in the case of, say, a cultivation temperature of 32° C., while the cis-isomers of monoacyl ester of said diol (II-C, II-D) that form concurrently exhibit a maximum value in 3–6 hours and disappear in 17–20 hours. On the other hand, about a half of the trans-isomers of the diacyl ester of said diol (I-A and I-B) disappear in about 12 hours, while the trans-isomers of monoacyl ester of said diol (II-A and II-B) that form concurrently exhibit a maximum value in about 12–15 hours.

As previously stated, the yeasts belonging to the *Saccharomyces* species and especially baker's yeast, hydrolyzes the (S)-trans-isomer at a higher rate than in the case of the (R)-trans-isomer, but this difference in hydrolysis rates also applies in the case of the diacyl esters of the trans-isomers and monoacyl ester of these trans-isomers.

Hence, in accordance with our researches, on observation of the hydrolysis of the trans-diesters in the hereinabove-described culture, it is seen that, say, in the case the culture was carried out for 17 hours, the composition of the diesters and monoesters of trans-isomers present in the culture medium became one in which the (R)-trans-isomers was considerably more rich than the (S)-trans-isomers. On the other hand, the composition of the diols becomes richer in (S)-trans-isomers. When the cultivation time is prolonged beyond 17 hours, the hydrolysis proceeds further and the amounts of diesters and monoesters of trans-isomers gradually decrease. On the other hand, the amount of trans-diols increases. For example, at about 30 hours, the composition of the diesters and monoesters in the culture medium becomes still more rich in (R)-trans-isomers, about 70–90% being such isomers. On the other hand, in the case of the composition of the diols, the ratio of (S)-trans-isomer to (R)-trans-isomers becomes still closer than that observed at the 17th hours of culture. This trend becomes still more pronounced as the cultivation time is prolonged.

As can be readily appreciated from the foregoing results, it becomes possible according to the invention process to obtain various optically active compounds, say, by suitable controlling the cultivation time.

As the cultivation time to be used in the invention process, about 12–120 hours is preferred, especially preferred being about 24–72 hours.

While the cultivation temperature may be any that will permit the yeast cells to survive, preferred is a temperature of 25°–45° C.

For enhancing the rate of conversion, it is preferred that the substrate such, for example, as the aforesaid diesters and monoesters be more uniformly dispersed in the culture liquid. In dispersing a water-insoluble substrate uniformly in the culture liquid, agitation of the culture liquid is preferably carried out. It is especially preferred to use either an agitating paddle or propeller and to vigorously agitate the culture liquid so as to disperse the substrate uniformly in the culture liquid as smaller size particles.

The isolation of the product can be readily carried out in usual manner. For example, the crude product can be readily obtained by extracting the product from the culture liquid with the usual organic solvents, for example, ethyl acetate, ether, chloroform, benzene, hexane and cyclohexane, and thereafter treating the extracts in customary manner. For carrying out the recovery of the product efficiently, it is desirable to employ the salting out operation and the continuous extraction method. The column chromatographic method or the preparative thin-layer chromatographic method is employed for purifying the crude product.

Again, the so isolated trans-diester or trans-monoester, whose optical activity has been enhanced, can be used as the starting material, or the aforesaid diol or monoester whose optical purity has been enhanced to a greater degree, after acylation by a suitable method and conversion to the monoester or diester thereof, can also be used as the starting material, and a still greater enhancement of their optical purity can be achieved by applying again the cultivation method of the present invention, following which they may be separated in like manner.

Thus, it becomes possible in accordance with the hereinbefore-described process of this invention to obtain at least one of the compounds (i) (R)-trans-diester (I-A), (ii) (R)-trans-monoester (II-A) and (iii) (S)-trans-diol (III-B), or said optically active diester, monoester or diol in which these at least one compound is contained in a still higher concentration.

These optically active compounds I-A, II-A and III-B obtained by the process of this invention are compounds that have not been reported heretofore in the literature, and we believe that these are new compounds and that we were the first to succeed in their production and separation.

Further, these compounds I-A, II-A and III-B prepared by the invention process are mutually convertible by methods which per se are known such, for example, as alkaline hydrolysis and acylation. The protected 4-hydroxycyclopent-2-en-1-one can be derived from these compounds by a suitable method. Next, when this protected 4-hydroxycyclopent-2-en-1-one is alpha, beta-dialkylated, a prostaglandin E type compound can be readily obtained.

2-1. The case where use is made of (A) the hydrolytic enzyme contained in the rind of citrus fruits or (B) the hydrolytic enzyme obtained from the filamentous fungus belonging to genus Aspergillus or its metabolic product When, in accordance with the present invention, a culture medium containing the aforementioned diacyl ester (I), a typical starting material, is inoculated with (A) the hydrolytic enzyme contained in the rind of citrus fruits or (B) the hydrolytic enzyme obtained from the filamentous fungus belonging to the genus Aspergillus or its metabolic product, it is possible by utilizing the difference in the hydrolysis rates of these enzymes (A) and (B) in hydrolyzing the acyloxy groups of the (R)- and (S)- configurations of said diacyl ester (I), especially its trans-isomers, e.g., the selectivity of the rates by which the enzymes hydrolyze these acyloxy groups, to accumulate in said culture medium at least one of the compounds of the group consisting of (i) (S)-trans-diester (I-B), (ii) (R)-trans-monoester (II-A) and (iii) 3(S)-acetoxy-5(R)-hydroxycyclopent-1-ene, i.e., the aforementioned 3(S)-cis-monoester (II-C).

Thus, it is possible according to this invention to separate and recover at least one of the foregoing compounds I-B, II-A and II-C by also using the foregoing enzyme (A) or (B) and by operating in the same manner as in the case where the aforesaid yeasts belonging to the *Saccharomyces* species are used. Again, it is also possible, if desired, to recover said diester composition or monoester composition containing at least on of these compounds in a higher concentration.

The enzyme known as citrus acetyl esterase is conveniently used as the foregoing hydrolytic enzyme (A) [see *Archiv. Biochem.*, 15, 415 (1947)].

The enzyme used in the enzymatic reaction can be used in the form of an enzyme obtained by the usual enzyme purification method, a crudely purified enzyme obtained by fractionation with ammonium sulfate or an organic solvent, or an crude enzyme such as a crushed product of the rinds of citrus fruits or an extract thereof.

On the other hand, as the foregoing hydrolytic enzyme (B), conveniently usable is the hydrolytic enzyme prepared from *Aspergillus Niger* ATTCC 9142. Thus, the hydrolytic enzymes used in these enzymatic reactions may be in any of such forms as the enzyme obtained by the usual enzyme purification method, the crudely purified enzyme obtained by, say, fractionation with ammonium sulfate or an organic solvent, or a crude enzyme such as a culture, culture liquid or cells or microorganisms, as well as the extracts thereof.

2-2 The case where use is made of the hydrolytic enzyme (C) contained in wheat germs According to this invention, it is also possible to inoculate a culture medium containing the aforesaid diacyl ester (I) with a hydrolytic enzyme (C) contained in wheat germ and by utilizing in like manner as previously described the selectivity in the hydrolytic rates, to accumulate in the culture medium at least one of the compounds of (i) (R)-trans-diester (I-A), (ii) (R)-trans-monoester (II-A) and (iii) 3(S)-cis-monoester (II-C).

Accordingly, the aforesaid optically active compounds of I-A, II-A and II-C can be isolated even when the foregoing enzyme (C) is used and by operating in the same manner as described hereinbefore. The diester or monoester compositions containing these compounds in a higher concentration can also be prepared.

As this enzyme (C), conveniently usable is, say, wheat germ lipase (Glycerol-ester Hydrolase EC No. 3.1.1.3). And an enzyme of any form prepared as in the case of the aforesaid *Aspergillus Niger* can also be used.

3. It is thus possible, according to this invention, to prepare a diester, monoester or diol containing at least one of the aforementioned optical isomers in a high concentration by inoculating the aforesaid diacyl ester (I) with either the yeasts of the *Saccharomyces* species described in 1, above, or the hydrolytic enzymes (A), (B), and (C) described in 2-1 and 2—2, above, after which these prepared diester, monoester or diol are separated from the culture medium. In the case of the diol, this can be converted to a diester or monoester by a suitable method as described hereinbefore, and, if desired, the monoester can be converted to a diester, which can then be again inoculated with either the foregoing yeasts or the hydrolytic enzyme (A), (B), or (C) to prepare a composition of still higher optical purity. That is to say, it is possible in accordance with this invention to carry out the invention process by suitably combining the foregoing yeasts or enzymes and carrying out the operation for the required number of times.

As the reaction solution with which the enzyme (A), (B) or (C) is inoculated, any which can retain the activity of the enzyme such as deionized water or a buffer solution may be used. For example, usable buffer solutions are those mentioned in *Data for Biochemical Research* by R. M. C. Dawson, D. C. Elliott, W. H. Elliott, and K. M. Gones; Oxford at the Clarendon Press, 1969. p 475. While as the ionic concentration of the buffer solution that which permits substantial enzymatic activity will do, preferred is a molar concentration of $1 \times 10^{-5} - 5.0$ M. On the other hand, as the pH of the reaction liquid, that which permits substantial enzymatic activity will do. Especially preferred is however a pH in the range or $\pm 2.0$ centering about the optimum pH of the enzyme used.

On the other hand, while the concentration of the substrate such, for example, as the diacyl ester (I) or the aforesaid monoester may be any concentration that permits substantial enzymatic activity, preferred is a concentration of the order of $1 \times 10^{-4} - 25.0\%$ by weight based on the reaction liquid, especially preferred being one of the order of $1 \times 10^{-3} - 5.0\%$ by weight.

The reaction time in which these enzymes are used is preferably one ranging, say, about 6–120 hours, but especially preferred is a time of 12–48 hours. As the reaction temperature, one that permits the enzymatic reaction to proceed will do, but preferred is a temperature of 25°–45° C. In enhancing the rate of hydrolysis of the starting material to the intended product in this invention, it is preferred that the substrate be dispersed as uniformly as possible in the reaction liquid, and hence agitation of the reaction liquid is preferably carried out to disperse uniformly the substrate which is a water-insoluble compound. It is especially preferred that an agitating paddle or propeller be used and that the agitation be carried out vigorously so as to achieve a uniform dispersion of the substrate in the reaction liquid as particles of smallest possible size.

As described in the case where yeasts are used (1, above), the isolation of the intended product can be readily carried out in customary manner by a method of extraction with an organic solvent or a method of separating the product by column chromatography using an ion-exchange resin or a synthetic absorbent. For example, the crude product of the intended cyclopentene derivative can be obtained by extracting the product from the reaction liquid with a usual organic solvent, e.g., ethyl acetate, ether, chloroform, benzene, hexane and cyclohexane, followed by treating the extracts in customary manner, such as removal of the solvent by evaporation.

For carrying out the recovery of the product with efficiency, the employment of the salting out operation and continuous extraction method is still more preferred. The purification of the crude product is carried out with the use of such methods as column chromatography, preparative thin-layer chromatography and preparative gas chromatography.

The yeasts such as the aforementioned baker's yeast are featured in that while the yield of the intended optically active product is generally low when these yeasts are used, the resulting product can be obtained as one of very high optical purity. On the other hand, the feature of the method which uses the aforementioned enzymes (A), (B) and (C) is that while the optical purity of the intended product is lower than that where the baker's yeast is used, the monoesters in which the aforesaid optical activity has been enhanced can be obtained in an exceedingly high yield. Further, there are such advantages as that since in the case of the method which uses these enzymes the purity of the enzyme can be enhanced, side reactions other than the intended hydrolysis can be checked and, in addition, it is possible to use these enzymes supported on a carrier material, i.e. immobilized enzymes.

Further, not only the (R)-trans-diester (I-A) and (R)-trans-monoester (II-A) that are obtained by the foregoing enzyme method but also the (S)-trans-diester (I-B) and 3(S)-cis-monoester (II-C) obtained by this method are new compounds, the isolation of which was first achieved by us. These compounds can also be converted to the prostaglandin E type compounds in the same manner as described in the section dealing with yeasts (1, above).

Again, as these compounds obtained by the invention process are optically active compounds, various other medicines, agricultural chemicals, perfumes, etc., can be synthesized therefrom.

The following examples will serve to further illustrate the invention, however, these examples are not to be construed as limiting the invention thereto. Unless otherwise specified, the parts are on a weight basis.

Method of determining the absolute configuration a. Determination of the absolute configuration of cyclopent-1-en-3,5-diol.

Baker's yeast was used, and the cultivation of the substrate 3,5-diacetoxycyclopent-1-en (mole ratio of cis-isomer to trans-isomer = 54:46) was carried out for 17 hours to obtain a product, which was separated by column chromatography to give cyclopent-1-en-3,5-diol (mole ratio of cis-isomer to trans-isomer = 55:63) exhibiting $[\alpha]_D^{20} = -44°$. The foregoing cis/trans ratios were determined by gas chromatography and NMR. The determination of the absolution configuration of the so obtained diol was carried out in the following manner.

This diol was first converted by a per se known method to dibenzoate, which was then converted to monobenzoate by alkaline hydrolysis. This was then converted to 4-benzoyloxycyclopent-2-en-1-one by oxidizing with chromic acid using acetone as solvent (the no changes occurred in the absolute configuration of the substituent-attached carbons as a result of the foregoing several reaction steps was ascertained in advance).

When the circular dichroism of the resulting product was observed, a negative cotton effect ($[\theta]_{226} = -47900°$ C, c = 3.2 × 10$^{-5}$) was observed. Hence, this product, which is known to exhibit negative chirality by the exciton chirality method [H. Harada and K. Nakanishi, *Accounts Chem. Res.*, 5, 257 (1972) and references cited therein], was found to have an S-configuration.

That is, it was found that the trans-isomer of cyclopent-1-en-3,5-diol exhibiting a negative value for the $[\alpha]_D^{20}$ value was of S-configuration. It is clear that the cis-isomer of this same diol is optically inactive.

b. Deterination of the absolute configuration of 3,5-acetoxycyclopent-1-ene and trans-3-acetoxy-5-hydroxycyclopent-1-ene.

Baker's yeast was used, and the cultivation of the substrate 3,5-diacetoxycyclopent-1-ene (mole ratio of cis-isomer to trans-isomer = 54:46) was carried out for 30 hours to obtain a product, which was separated by column chromatography to give trans-3,5-diacetoxycyclopent-1-ene exhibiting a $[\alpha]_D^{20} = +199°$ and trans-3-acetoxy-5-hydroxycyclopent-1-ene exhibiting a $[\alpha]_D^{20} = +199°$. Using these compounds, their absolute configurations were determined in the following manner.

When the foregoing trans-3,5-diacetoxycyclopent-1-ene was alkaline hydrolyzed by a per se known method and converted to trans-cyclopent-1-en-3,5-diol, it exhibited a $[\alpha]_D^{20} = +186°$ C. Hence, the trans-cyclopent-1-en-3,5-diol exhibiting a positive specific rotation was found to have an absolute configuration opposite to that of the trans-isomer which exhibits a negative specific rotation. [that there was no change in the absolute configuration of the substitutent-attached carbon during the foregoing step of alkaline hydrolysis is shown in *Helv. Chim. Acta*, 53, 739 (1970)].

It was therefore found that the foregoing trans-isomer of 3,5-diacetoxycyclopent-1-ene exhibiting a positive specific rotation was of R-configuration.

When a similar operation was carried out on the foregoing trans-3-acetoxy-5-hydroxycyclopent-1-ene, the corresponding diol exhibiting a positive specific rotation was obtained. Hence, this compound was found to be of R-configuration.

c. Determination of the absolute configuration of cis-3-acetoxy-5-hydroxycyclopent-1-ene.

The trans-3-acetoxy-5-hydroxycyclopent-1-ene obtained by using baker's yeast and whose absolute configuration was determined to be of R-configuration was converted to 4-acetoxycyclopent-2-en-1-one by oxidation with chromic acid. When the specific rotation of this compound was found to be +74°.

Separately, the cultivation of the substrate 3,5-diacetoxycyclopent-1-ene (mole ratio of cis-isomer to trans-isomer = 54 : 46) was carried out for 22 hours using citrus acetyl estrase to obtain a product, which was separated by column chromatography to obtain 3-acetoxy-5-hydroxycyclopent-1-ene. This was further submitted to gas chromatography to separate and obtain the cis-isomer only. This cis-3-acetoxy-5-hydroxycyclopent-1-ene was oxidized similarly as described above to give 4-acetoxycyclopent-2-en-1-one whose specific rotation was −15°.

Hence, when the foregoing two operations are compared, it is seen that the 3-position of the foregoing cis-3-acetoxy-5-hydroxycyclopent-1-ene, i.e.) the carbon to which the acetoxy group is attached, has a S-configuration, and thus the compound was determined to be cis-3(S)-acetoxy-5-(R)-hydroxycyclopent-1-ene.

Method of determining the optical purity

The NMR of trans-3-acetoxy-5-hydroxycyclopent-1-ene of $[\alpha]_D^{20} = +229°$ obtained by using a culture of 3,5-diacetoxycyclopent-1-ene with baker's yeast was measured in the presence of tris-(3-trifluoromethylhydroxymethylene-d-camphorato)europium (III) [see C. C. Hinckley, *J. Am. Chem. Soc.*, 91, 5160 (1969) and G. M. Whitesides, D. W. Lewis ibid, 92, 6979 (1970)]. As a result, it was found that two classes of optically active compounds were present in a ratio of 95:5. This shows the presence of one of the enantiomer in an amount of 90% enantiomeric excess. Hence, the maximum specific rotation of the trans-acetate is 255°.

On the other hand, the foregoing trans-monoacetate of $[\alpha]_D^{20} = +229°$ (90% e.e.) was acetylated and converted to trans-3,5-diacetoxycyclopent-1-ene which exhibited a $[\alpha]_D^{20} = +208°$. Hence, the maximum specific rotation of the trans-diacetate becomes 231°.

Further, the cyclopent-1-en-3,5-diol (cis-isomer: trans-isomer = 34:66) of $[\alpha]_D^{20} = -81°$ (based on the trans-isomer) separated in the cultivation of 3,5-diacetoxycyclopent-1-ene with baker's yeast was similarly converted to a diacetylated product in a customary manner. This exhibited a $[\alpha]_D^{20} = -73°$. Hence, the maximum specific rotation of the trans-diol becomes 237°.

Using the maximum specific rotation of those obtained diacetate, monoacetate and diol that have been calculated as above described, the optical purities (% e.e.) of the several compounds separated in the several cases can be calculated by measurement of their specific rotations ($[\alpha]_D^{20}$).

EXAMPLE 1

THE CASE WHERE BAKER'S YEAST WAS USED

1. Culture (48-hour cultivation)

270 grams of commercial baker's yeast (compressed cake produced by Oriental Kobo Kogyo Co., Ltd.), 90 grams of glucose, 67.5 grams of monobasic sodium phosphate and 1.8 liters of deionized water were placed in a 5-liter separable round-bottomed flask and, after being rendered into a homogeneous solution, left to stand for one hour at room temperature. To this solution was then added 18 grams of 3,5-diacetoxycyclopent-1-ene(cis-isomer: trans-isomer ratio = 54:46) as a substrate, following which it was cultivated for 48 hours at 32° C. with vigorous stirring with an agitating propeller.

2. Separation and purification of the product

After completion of the culture, the cells were separated from the culture liquid using a centrifuge. After adding ammonium sulfate to the supernatant liquid, it was submitted to a salting out operation and then extracted five times using 2 liters of ethyl acetate on each occasion. The so obtained extracts were combined with the extract obtained by extracting the cells separately with ethyl acetate, after which the combined extract was dried with Glauber's salt. The solvent was then distilled off to obtain 7.23 grams of a crude product.

When this product was submitted to thin-layer chromatography (developing solvent: a mixture of 50 parts of ethyl acetate and 50 parts of benzene), spots were exhibited principally at Rf = 0.58, 0.25 and 0.04 as a result of the culture.

When this crude product was purified and collected by dry column chromatography, 132 mg (yield 0.6%) of a liquid corresponding to Rf = 0.58, 520 mg (yield 3.2%) of a liqud corresponding to Rf = 0.25, and 2.62 g (yield 25.2%) of a liquid corresponding to Rf = 0.04 were obtained.

3. Identification of the product

The properties of the liquid corresponding to Rf = 0.58 were as follows:

IR (liquid film, cm$^{-1}$): 1735, 1240, 1035

NMR (60 MHz, CCl$_4$, ppm): 2.00 (6H, s), 2.21 (2H, t, J = 6Hz), 5.73 (2H, t. J = 6Hz), 6.06 (2H, s)

Mass (70eV, m/e, %): 141 (M$^+$ - COCH$_3$, 2), 125 (73), 124 (65), 99 (27), 82 (100), 43 (80) $[\alpha]_D^{20} = +215°$ (C = 0.023, CH$_3$OH)

These properties confirm that this product is (R)-trans-3,5-diacetoxycyclopent-1-ene (93% e. e.).

The properties of the liquid corresponding to Rf = 0.25 are as follows:

IR (liquid film, cm$^{-1}$): 3350, 1730, 1430, 1375, 1355, 1250, 1150, 1120

NMR (60 MHz, CCl$_4$, ppm): 2.00 (3H, s), 2.10 (2H, m), 4.35 (1H, s), 4.90 (1H, m) 5.75 (1H, m), 6.00 (2H, m)

Mass (70eV, m/e, %): 99(M$^+$ - COCH$_3$, 3), 82 (100), 43 (80) $[\alpha]_D^{20} = +258°$ (C = 0.032, CH$_3$OH)

That this product is 3(R)-acetoxy-5(R)-hydroxycyclopent-1-ene (100% e. e.) is confirmed by these properties.

The spectral data of IR, NMR and Mass of the liquid corresponding to Rf = 0.04 were in agreement with those of a authentic cyclopent-1-en-3,5-diol, a known compound. Hence, this liquid was identified as being cyclopent-1-en-3,5-diol. Further, this cyclopent-1-en-3,5-diol was found to have a cis-isomer to trans-isomer ratio of 17:9 and a $[\alpha]_D^{20} = -15°$ (C=0.072, CH$_3$OH), and its optical parity was 10% e.e.

EXAMPLES 2–5

CASES WHERE BAKER'S YEAST WAS USED

Example 1 was repeated, except that incubation times of 30, 17, 10 and 5 hours were used. The separation and purification of the product and confirmation thereof were carried out in exactly the same manner.

The results obtained are shown in Table 1.

Table 1

| Example No. | Incubation time (hr). | 3,5-Diacetoxy-cyclopent-1-ene Yield (%) | $[\alpha]_D^{20}$ (% e.e.) | 3-Acetoxy-5-hydroxycyclopent-1-ene Yield (%) | $[\alpha]_D^{20}$ (% e.e.) | 3,5-Dihydroxy-cyclopent-1-ene Yield (%) | $[\alpha]_D^{20}$ (% e.e.) |
|---|---|---|---|---|---|---|---|
| 2 | 30 | t. 2.5<br>c. 0 | +199° t. 5.4<br>(86) c. 0 | +199° t 8.2<br>(78) c. 2.1 | | −37°<br>(19) | |
| 3 | 17 | t. 9.1<br>c. 0 | +185° t. 11.5<br>(80) c. 0 | +143° t. 6.3<br>(56) c. 5.5 | | −44°<br>(32) | |
| 4 | 10 | t. 14.9<br>c 1.1 | + 45° t. 6.2<br>(21) c. 4.7 | ± 0° t. 3.9<br>c. 6.7 | | −24°<br>(28) | |
| 5 | 5 | t. 16.8<br>c. 10.8 | + 8° t. 1.7<br>(6) c. 7.0 | − 17° trace | | — | |

In the table "t" and "c" denote cis-isomer and trans-isomer, respectively. The ratio of trans-isomer to cis-isomer was determined by gas chromatography

EXAMPLE 6

The case where baker's yeast was used

Operating as in Example 1, 300 grams of the same commercial baker's yeast used therein, 100 grams of glucose, 75 grams of monobasic sodium phosphate and 2.0 liters of deionized water were placed in a 5-liter separable round-bottomed flask and, after being rendered into a homogeneous solution, left to stand for one hour at room temperature. To this solution was then added 20 grams of 3,5-diacetoxycyclopent-1-ene (cis-isomer to trans-isomer ratio = 54:46) as a subtrate, after which the cultivation was carried out for 30 hours at 32° C. with vigorous stirring using an agitating propeller. After completion of the culture, the cells were separated from the culture liquid by centrifugation followed by extracting the culture liquid with ethyl acetate as in Example 1 to obtain 9.13 grams of a crude product.

When this crude product was purified by column chromatography, 932 mg of 3(R)-acetoxy-5(R)-hydroxycyclopent-1-ene (80% e. e.) exhibiting a $[\alpha]_D^{20} = +208°$ (C= 0.062, $CH_3OH$) and 1.62 grams of cyclopent-1-en-3,5-diol (31% e. e.) of cis-isomer to trans-isomer ratio =3:7 exhibiting a $[\alpha]_D^{20} = -46°$ (C=0.065, $CH_3OH$) were obtained.

EXAMPLE 7

The case where baker's yeast was used

Operating as in Example 1, 300 grams of the same commercial baker's yeast was used in therein, 100 grams of glucose, 75 grams of monobasic sodium phosphate and 2.0 liters of deionized whater were placed in a 5-liter separable round-bottomed flask and, after being rendered into a homogeneous solution, left to stand for one hour at room temperature. To this solution was then added 20 grams of 3,5-diacetoxycyclopent-1-ene(cis-isomer to trans-isomer ratio = 54:46) as substrate, after which the cultivation was carried out for 17 hours at 32° C. with vigorous stirring using an agitating properller. After completion of the culture, extraction with ethyl acetate was carried out as in Example 1 to obtain 10.23 grams of a crude product.

When this crude product was purified by column chromatography, 1.93 grams of (R)-trans-3,5-diacetoxycyclopent-1-ene (86% e. e.) exhibiting a $[\alpha]_D^{20} = +201°$ (C= 0.081, $CH_3OH$), 2.08 grams of 3(R)-acetoxy-5(R)-hydroxycyclopent-1-ene (73% e.e.) exhibiting a $[\alpha]_D^{20} = +192°$ (C=0.069, $CH_3OH$) and 1.33 grams of cyclopent-1-en-3,5-diol of cis-isomer to trans-isomer ratio = 5:6 (37% e. e.) exhibiting a $[\alpha]_D^{20} = -53°$ (C=0.061, $CH_3OH$) were obtained.

EXAMPLE 8

The case where baker's yeast was used

Operating as in Example 1, 30 grams of the same commercial baker's yeast used therein, 10 grams of glucose, 7.5 grams of monobasic sodium phosphate 200 ml of deionized water and 3.0 grams of 3,5-diacetoxycyclopent-1-ene as substrate were placed in a mini-jar, after which the culture was carried out for 24 hours at 32° C. while stirring with an agitating propeller. After completion of the culture, the culture liquid was extracted with ethyl acetate and dried with Glauber's salt. On removal of the solvent by distillation, 2.1 grams of a crude product was obtained.

This crude product was submitted as in Example 1 to thin-layer chromatography (developing solvent: a mixture of 50 parts of ethyl acetate and 50 parts of benzene), and the portion exhibiting Rf=0.25 was scraped off to obtain 95 mg of 3(R)-acetoxy-5(R)-hydroxycyclopent-1-ene.

EXAMPLE 9

The case where citrus acetyl esterase was used

1. Preparation of the citrus acetyl esterase

The rinds of mandarin orange were crushed in a mixer, extracted with a 0.2% aqueous sodium chloride solution and centrifuged to separate and removed the rind residue. The supernatant liquid was saturated with ammonium sulfate to precipitate a protein fraction, which was collected by centrifugation. This protein fraction was dialyzed against deionized water. The resulting enzyme solution was used, as obtained, as the citrus acetyl esterase solution in the following culture reaction.

2. Culture 20 ml of the foregoing enzyme solution, 3.0 grams of 3,5-diacetoxycyclopent-1-ene as a substrate, and 180 ml of a 0.05 M sodium phosphate buffer solution of pH 7.0 were suspended in a 1-liter Erlenmeyer flask and reacted for 22 hours at 32° C. with vigorous stirring using an agitating paddle.

3. Separation and purification of the product

After completion of the reaction, the reaction liquid was extracted with about 200 ml of ethyl acetate and then dried with Glauber's salt. The solvent was then distilled off to obtain 2.97 grams of a crude product. When a very small part of this product was submitted to thin-layer chromatography (developing solvent: a mixture of 50 parts of ethyl acetate and 50 parts of benzene), spots were exhibited at Rf = 0.54 and Rf = 0.27.

This crude product was then submitted to column chromatography using silica gel. By carrying out the elution by the concentration gradient elution method using 50 parts of benzene and 50 parts of ethyl acetate, 1.49 grams of a product corresponding to Rf = 0.54 and 0.91 gram of a product corresponding to Rf=0.27 were obtained.

4. Confirmation of the product

As the product corresponding to Rf = 0.54 was in agreement with the separately prepared authentic 3,5-diacetoxycyclopent-1-ene with respect to its IR, NMR and Mass, it was identified as being 3,5-diacetoxycyclopent-1-ene. This product exhibited a $[\alpha]_D^{20} = -7.4°$.

In the case of the product corresponding to Rf = 0.27, since this product was in agreement as to its IR, NMR and Mass with the product corresponding to Rf= 0.24 obtained by the method of Example 1, it was identified as being 3-acetoxy-5-hydroxycyclopent-1-ene. This product exhibited a $[\alpha]_D^{20} = +7.7°$.

Further, since both products were found to be mixtures of the cis-isomer and trans-isomer according to gas chromatography, for determining the absolute configuration, the 3-acetoxy-5-hydroxycyclopent-1-ene was separated by gas chromatography (ratio of cis-isomer to trans-isomer = 56 : 44). Since it is clear that the cis-3,5-diacetoxycyclopent-1-ene is optically inactive, the separation of the above-obtained 3,5-diacetoxycyclopent-1-ene (ratio of cis-isomer to trans-isomer = 54:46) was not carried out, but from the foregoing $[\alpha]_D^{20}$ value the trans-isomer was found to be of S-configuration, and its optical purity was found to be 7% e. e.

On the other hand, the trans-3-acetoxy-5-hydroxycyclopent-1-ene and the cis-3-acetoxy-5-hydroxycyclopent-1-ene was obtained by separation exhibited the $[\alpha]_D^{20} = +21°$ and $[\alpha]_D^{20} = -15°$, respectively. Hence, it was found that the trans-isomer was of R-configuration and its optical purity was 8% e. e. and that the cis-isomer was 3(S)-acetoxy-5(R)-hydroxycyclopent-1-ene.

EXAMPLE 10

The case where citrus acetyl esterase was used 2.0 ml of the enzyme solution prepared by the method of (1) of Example 9, 101 mg of 3,5-diacetoxycyclopent-1-ene as substrate and 2.0 ml of a 0.05 M sodium phosphate buffer solution of pH 7.0 were suspended and reacted overnight at 32° C. with vigorous stirring using an agitating paddle. After completion of the reaction, the extraction was carried out as in (3) of Example 9 followed by drying the extract with Glauber's salt and removal of the solvent by distillation to obtain 89 mg of a crude product. This product was purified by preparative thin-layer chromatography using a mixture of 50 parts of ethyl acetate and 50 parts of benzene to obtain 40 mg of a liquid of Rf = 0.54 and 35 mg of a liquid of Rf = 0.27.

Since in the case of both compounds their IR's, NMR's and Masses were in agreement with those of the compounds exhibiting the same Rf values obtained by the method of Example 9, the compound exhibiting Rf = 0.54 was found to be 3,5-diacetoxycyclopent-1ene, while the compound exhibiting Rf = 0.27 was found to be 3-acetoxy-5-hydroxycyclopent-1-ene.

The $[\alpha]_D^{20}$ of the foregoing 3,5-diacetoxycyclopent-1-ene was about −6°, while the $[\alpha]_D^{20}$ of the foregoing monoacetate was about +4°.

EXAMPLE 11

The case where the cells of the genus *Aspergillus niger* were used

1. Preparation of the crude enzyme solution

Five platinum loopful of *Aspergillus niger* ATCC 9142 was cultivated for 72 hours at 30° C. in 2.5 liters of culture liquid having the composition (per liter) of 20 grams of glucose, 1.5 grams of monopotassium phosphate, 1.5 grams of magnesium sulfate heptahydrate, 1.0 gram of ammonium nitrate, 1.0 gram of lactoalbumin, 2.0 grams of corn steep liquor (liquid), 0.5 gram of yeast extract powder, 0.5 gram of L-glutamic acid and 10 mg of zinc sulfate heptahydrate, and adjusted to pH 7 with 30% caustic soda. This was followed by sonication of the broth. The fraction salted out with 0.35 − 0.6 ammonium sulfate was then obtained in accordance with the method of Fukumoto et al. [*J. Gen. Appln. Microbiol.*, 9, 353 (1973)] and this was used as the crude enzyme solution in the following culture.

2. Culture

Three ml of the foregoing crude enzyme solution and 200 mg of 3,5-diacetoxycyclopent-1pene as substrate were suspended in 6.0 ml of a phosphoric acid buffer solution of 0.1 mol concentration (pH = 5.6), and reacted at 32° C for 24 hours with vigorous stirring using an agitating paddle.

3. Separation and purification of the product

After completion of the reaction, the reaction mixture was extracted five times using 10 ml of ethyl acetate on each occasion, following which the extracts were combined and dried with Glauber's salt. On removal of the solvent by distillation, 100 mg of a crude product was obtained. When a very small portion of this was analyzed by thin-layer chromatography (developing solvent: a mixture of 50 parts of ethyl acetate and 50 parts of benzene), spots were exhibited at Rf = 0.58 and Rf = 0.25.

When this crude product was submitted to preparative thin-layer chromatography (developing solvent: a mixture of 50 parts of ethyl acetate and 50 parts of benzene), 63 mg of a compound corresponding to Rf = 0.58 and 38 mg of a compound corresponding to Rf = 0.25 were obtained.

4. Confirmation of the product

The IR's, NMR's and Masses of the compound corresponding to Rf = 0.58 and the compound corresponding to Rf = 0.25 were in agreement with those of 3,5-diacetoxycyclopent-1-ene and 3-acetoxy-5-hydroxycyclopent-1-ene, respectively.

The foregoing diacetate and monoacetate exhibited a $[\alpha]_D^{20} = -30°$ and a $[\alpha]_D^{20} = +107°$, respectively, and both compounds were found to be a mixture of cis-isomer and trans-isomer by gas chromatography. Hence, for determining the absolute configurations, the monoacetate was separated by gas chromatography (cis-isomer to trans-isomer ratio = 47:53).

Since it is clear that cis-diacetate is optically inactive, the separation of the diacetate (cis-isomer to trans-isomer ratio = 62:38) was not conducted, and it was found from its foregoing $[\alpha]_D^{20}$ value that the trans-isomer contained therein was of S-configuration, and that its optical purity was 34% e.e.

Further, since the trans-monoacyl compound and cis-monoacyl compound obtained by separation exhibited a $[\alpha]_D^{20} = +210°$ and $[\alpha]_D^{20} = -9°$, respectively, the trans-monoacyl compound was found to be of R-configuration and of 81% e.e., while the cis-monoacyl compound was found to be 3(S)-acetoxy-5(R)-hydroxycyclopent-1-ene.

EXAMPLE 12

The case where *Aspergillus niger* was used 3.0 ml of a crude enzyme solution of *Aspergillus niger* prepared as in (1) of Example 11 and 213 mg of 3-acetoxycyclopent-1-ene as substrate were suspended in 6.0 ml of an acetic acid buffer solution of 0.05 molar concentration and pH 5.6. The reaction was then carried out for 24 hours at 32° C. with vigorous stirring using an agitating paddle. After completion of the reaction, the reaction mixture was extracted with ethyl acetate as in Example 11 followed by drying the extract with Glauber's salt. On removal of the solvent by distillation, 65 mg of a crude product was obtained.

This crude product was analyzed by thin-layer chromatography as in (3) of Example 11 to obtain 35 mg of a compound corresponding to Rf = 0.58 and 23 mg of a compound corresponding to Rf = 0.25.

From the respective Rf values of these compounds the former was found to be 3,5-diacetoxycyclopent-1-ene while the latter was found to be 3-acetoxy-5-hydroxycyclopent-1-ene.

The $[\alpha]_D^{20}$ value of the former was about −25°, while the $[\alpha]_D^{20}$ value of the latter was about +87°.

EXAMPLE 13

The case where wheat germ lipase was used

1. Culture 50 mg of commercial Wheat Germ Lipase Type 1 (glycerol-ester hydrolase) EC No. 3.1.1.3 (produced by Sigma Chemical Co.) and 300 mg of 3,5-diacetoxycyclopent-1-ene as substrate were suspended in 100 ml of an acetic acid buffer solution of 0.1 molar concentration and pH 5.0, and the reaction was carried out for 24 hours at 32° C. with vigorous stirring using an agitating paddle.

2. Separation and purification of the product

After completion of the reaction, the reaction product was extracted five times using 100 ml of ethyl acetate on each occasion, following which the extract was dried with Glauber's salt. The solvent was then distilled off to obtain 270 mg of a crude product.

When a very small portion of this product was analyzed by thin-layer chromatography (developing solvent: a mixture of 50 parts of ethyl acetate and 50 parts of benzene), spots were exhibited at Rf = 0.58 and Rf = 0.25.

When this crude product was then separated by preparative thin-layer chromatography using the same developing solvent as that used above, 190 mg of a compound corresponding to Rf = 0.58 and 70 mg of a compound corresponding to Rf = 0.25 were obtained.

3. Confirmation of the product

The compound corresponding to Rf = 0.58 and that corresponding to Rf = 0.25 were found from their IR's, NMR's and Masses to be respectively 3,5-diacetoxycyclopent-1-ene and 3-acetoxy-5-hydroxycyclopent-1-ene.

The specific rotations $[\alpha]_D^{20}$ of the foregoing diacetate and monoacetate were +49° and +3°, respectively and, according to a gas chromatographic analysis, these were found to be mixture of cis- and trans-isomers.

That is, from the fact that the ratio of cis-isomer to trans-isomer of the diacetate is 28:12 and that the cis-isomer is optically inactive, it was found from the foregoing $[\alpha]_D^{20}$ value that the trans-isomer contained in the diacetate was of R-configuration and of 70% e. e.

On the other hand, the ratio of cis-isomer to trans-isomer of the monoacetate was 88:70. This monoacetate was acetylated by a known procedure and converted to a diacetate. From the fact that this exhibited a $[\alpha]_D^{20} = +9°$, the trans-monoacetate of the foregoing monoacetate was found to be of R-configuration and of 4% e.e.

Further, the foregoing monoacetate was oxidized with chromic acid in acetone and transformed to 4-acetoxycyclopent-2-en-1-one. From the fact that this compound exhibited a $[\alpha]_D^{20} = -1°$, it was concluded that the following inequality exists between the optical isomers of cis-isomer and trans-isomer of the foregoing monoacetate; that is, (S)-trans-monoacetate - 3(S)-acetoxy-5(R)-hydroxycyclopent-1-ene > (R)-trans-monoacetate + 3(R)-acetoxy-5(S)-hydroxycyclopent-1-ene.

Further, when the fact that (R) - trans-monoacetate > (S)-trans-monoacetate, as above indicated, is taken into consideration, then 3(S)-acetoxy-5(R)-hydroxycyclopent-1-ene > 3(R)-acetoxy-5(S)-hydroxycyclopent-1-ene holds good.

Accordingly, it was found that the cis-monoacetate was 3(S)-acetoxy-5(R)-hydroxycyclopent-1-ene.

EXAMPLE 14

The case where wheat germ lipase was used

Using as substrate 1.0 gram of the 3,5-diacetoxycyclopent-1-ene of $[\alpha]_D^{20} = -7.4°$ obtained in Example 9, the culture and separation and purification of the product was carried out as in (1) of Example 13 to obtain 250 mg of a compound corresponding to Rf = 0.58, i.e., 3,5-diacetoxycyclopent-1-ene and 325 mg of a compound corresponding to Rf = 0.25, i.e., 3-acetoxy-5-hydroxycyclopent-1-ene.

The $[\alpha]_D^{20}$ of the diacetate was +26°, while that of the monoacetate was +5°. On the other hand, the ratio of cis-isomer to trans-isomer in the case of the diacetate was 72:25 and in the case of the monoacetate was 60:40. It was thus found that the optical purity of the former was 45% e.e.

It can be seen from the foregoing results that when an optically inactive 3,5-diacetoxycyclopent-1-ene is used as the substrate, and a repetitive cultivation procedure is carried out wherein the substrate is first subjected to the action of citrus acetyl esterase and thereafter the resulting diacetate of enhanced optical activity is subjected to the action of wheat germ lipase, it becomes possible to obtain a diacetate and a monoacetate having much higher optical activities.

What we claim is:

1. A process for converting a diacyl ester of cyclopent-1-en-3,5-diol to its monoacyl ester and/or its diol which comprises subjecting a diacyl ester of cyclopent-1-en-3,5-diol of the formula

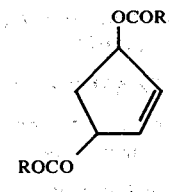

wherein R is a monovalent hydrocarbon residue of 1–10 carbon atoms, said diacyl ester of cyclopent-1-en-3,5-diol containing at least one member of the group consisting of
 1. a diacyl ester of (R)-trans-cyclopent-1-en-3,5-diol,
 2. a diacyl ester of (S)-trans-cyclopent-1-en-3,5-diol, and
 3. a diacyl ester of cis-cyclopent-1-en-3,5-diol,
to the action of a microorganism or enzyme having a selectivity in its rate of hydrolyzing the acyloxy group of (R) configuration and the acyloxy group of (S) configuration of said diacyl ester, selected from the group consisting of a yeast of the species Saccharomyces, a hydrolytic enzyme contained in the rinds of citrus fruits, a hydrolytic enzyme obtained from the filamentous fungus of the genus Aspergillus, or a hydrolytic enzyme contained in wheat germ.

2. The process of claim 1 carried out in a nutrient medium.

3. The process of claim 1 wherein the species Saccharomyces is used.

4. The process of claim 1 wherein the enzyme is the hydrolytic enzyme obtained from the filamentous fungus of the genus Aspergillus.

5. The process of claim 1 wherein the enzyme is the hydrolytic enzyme contained in wheat germ.

6. A process according to claim 1 whereby cis-cyclopent-1en-3,5-diol or its monoacyl ester is accumulated in a nutrient medium and wherein said diacyl ester of cyclopent-1-en-3,5-diol consists of a diacyl ester of cis-cyclopent-1-en-3,5-diol.

7. The process of claim 1 wherein the R in said formula is an alkyl radical of 1–5 carbon atoms.

8. The process of claim 1 wherein the R in said formula is methyl.

9. The process of claim 1 wherein said microorganism is an active strain of the *Saccharomyces cerevisiae* species.

10. The process of claim 1 wherein said enzyme is selected from the group consisting of citrus acetyl esterase, the active strains of *Aspergillus niger*, and wheat germ lipase.

* * * * *